United States Patent
Tsubouchi

(10) Patent No.: US 11,364,090 B2
(45) Date of Patent: Jun. 21, 2022

(54) ARTICULATING STABILIZER ARM WITH ADJUSTABLE LENGTH

(71) Applicant: TERUMO CARDIOVASCULAR SYSTEMS CORPORATION, Ann Arbor, MI (US)

(72) Inventor: Takeshi Tsubouchi, Dexter, MI (US)

(73) Assignee: TERUMO CARDIOV ASCULAR SYSTEMS CORPORATION, Ann Arbor, MI (US)

( * ) Notice: Subject to any disclaimer, the term of this patent is extended or adjusted under 35 U.S.C. 154(b) by 281 days.

(21) Appl. No.: 16/826,593

(22) Filed: Mar. 23, 2020

(65) Prior Publication Data

US 2020/0214792 A1 Jul. 9, 2020

Related U.S. Application Data

(63) Continuation of application No. PCT/US2018/052842, filed on Sep. 26, 2018.
(Continued)

(51) Int. Cl.
*A61B 90/50* (2016.01)
*A61B 17/02* (2006.01)
*A61B 17/00* (2006.01)

(52) U.S. Cl.
CPC .............. *A61B 90/50* (2016.02); *A61B 17/02* (2013.01); *A61B 2017/00991* (2013.01)

(58) Field of Classification Search
CPC .................... A61B 90/50; A61B 17/02; A61B 2017/00991; A61B 2017/0243
(Continued)

(56) References Cited

U.S. PATENT DOCUMENTS 4,457,300 A 7/1984 Budde
6,102,853 A * 8/2000 Scirica ............... A61B 17/0293
600/234
(Continued)

FOREIGN PATENT DOCUMENTS

DE 102011114633 A1 4/2013

OTHER PUBLICATIONS

International Search Report, PCT/US2018/052842, dated Aug. 1, 2019.

*Primary Examiner* — Kevin T Truong
*Assistant Examiner* — Tracy L Kamikawa
(74) *Attorney, Agent, or Firm* — Darryl Newell; MacMillan, Sobanski & Todd, LLC

(57) ABSTRACT

A reusable flexible arm stabilizes tissues during surgical procedures. The stabilizer arm switches between a flexible state for conforming to a desired curvature and a rigid state for maintain a desired positioning. A suspension length provided by the stabilizer arm is also adjustable. The arm has an articulating portion with successive articulating links each having a central passage. A length adjustable portion has successive length-adjustable links each having a central passage. A tension cable extends through the central passages between a proximal one of the length-adjustable links and a distal one of the articulating links. A base member captures the length-adjustable links at a position corresponding to a desired extension length of the arm. A control mechanism is movable between a retracted position and an extended position to selectably separate the captured length-adjustable links, thereby adjusting a tension in the tension cable and a rigidity of the stabilizer arm.

12 Claims, 12 Drawing Sheets

Related U.S. Application Data

(60) Provisional application No. 62/565,342, filed on Sep. 29, 2017.

(58) Field of Classification Search
USPC .......................................................... 600/229
See application file for complete search history.

(56) References Cited

U.S. PATENT DOCUMENTS

| | | | |
|---|---|---|---|
| 6,338,738 B1* | 1/2002 | Bellotti | F16M 11/40 |
| | | | 606/232 |
| 6,581,889 B2* | 6/2003 | Carpenter | A61B 17/02 |
| | | | 248/231.71 |
| 6,860,668 B2 | 3/2005 | Ibrahim et al. | |
| 8,498,198 B2 | 7/2013 | Kim et al. | |
| 9,486,296 B2 | 11/2016 | Mire et al. | |
| 2004/0242969 A1* | 12/2004 | Sherts | A61B 17/0293 |
| | | | 600/231 |
| 2007/0261320 A1 | 11/2007 | Lucas | |
| 2009/0216232 A1* | 8/2009 | Buford, III | A61B 17/7208 |
| | | | 29/244 |
| 2012/0010629 A1* | 1/2012 | Mire | A61B 17/29 |
| | | | 606/130 |
| 2016/0091138 A1* | 3/2016 | Agbodoe | F16M 11/40 |
| | | | 248/276.1 |

\* cited by examiner

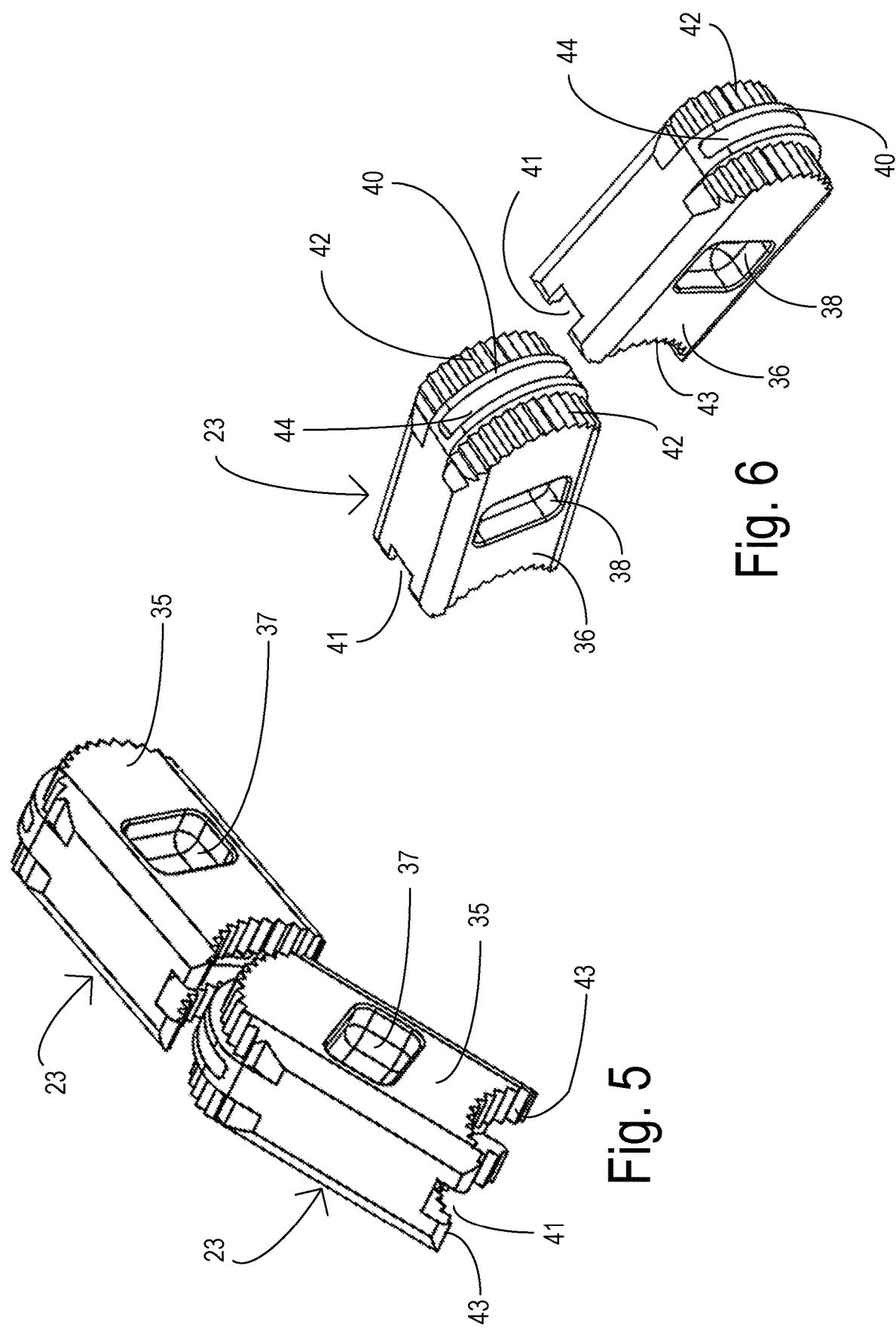

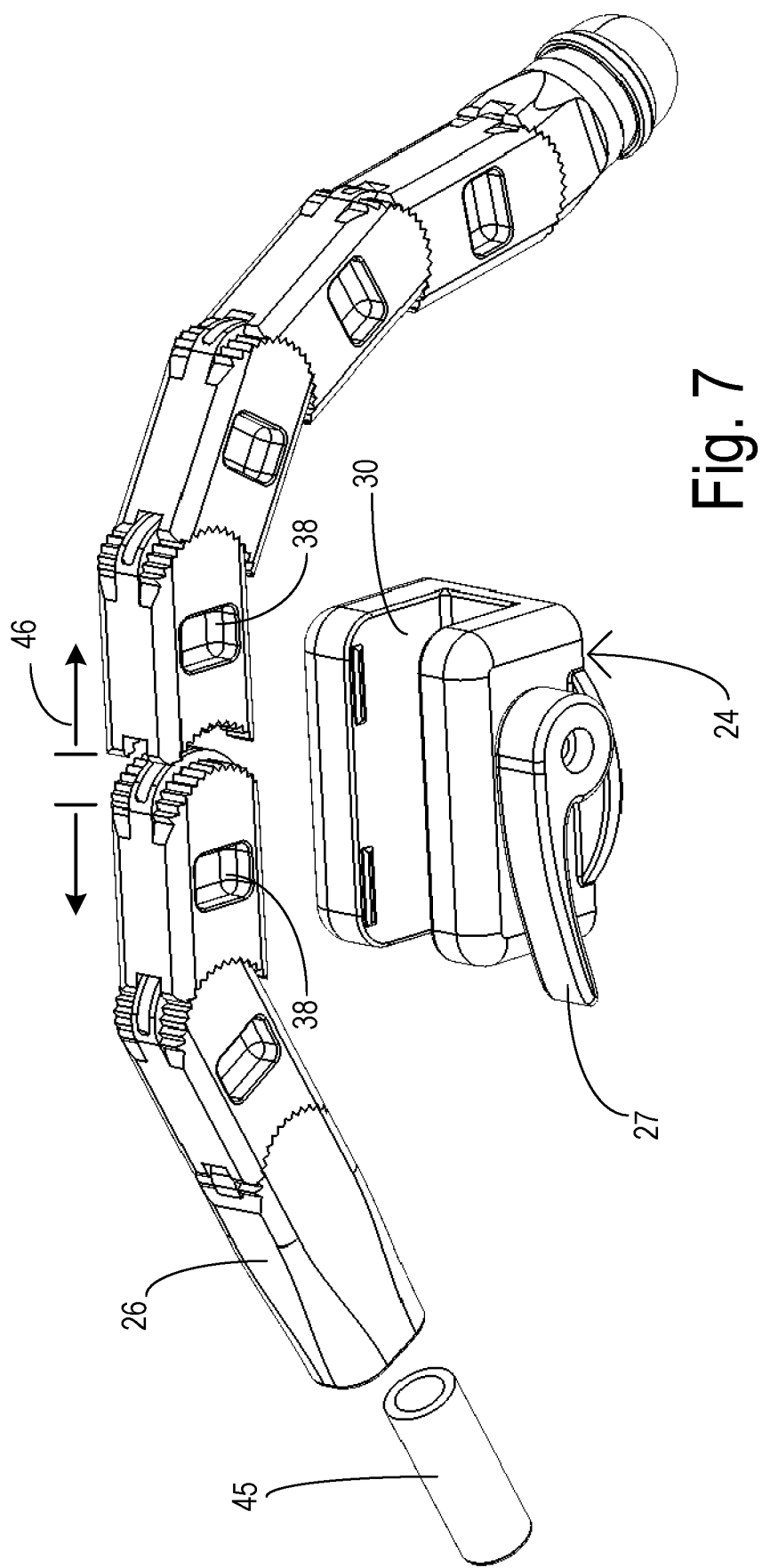

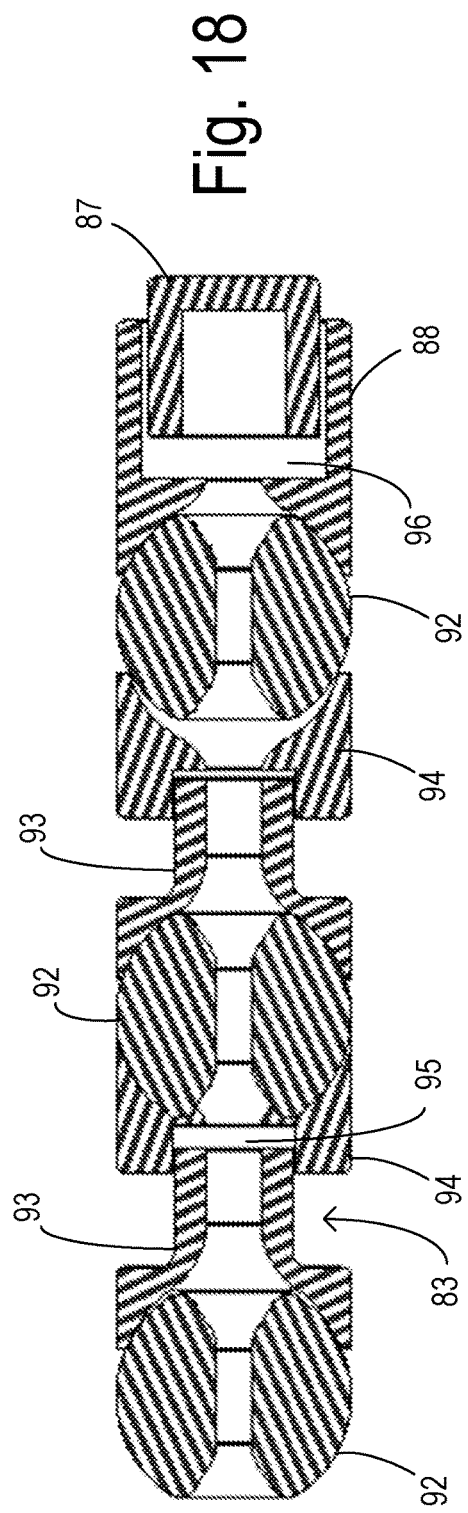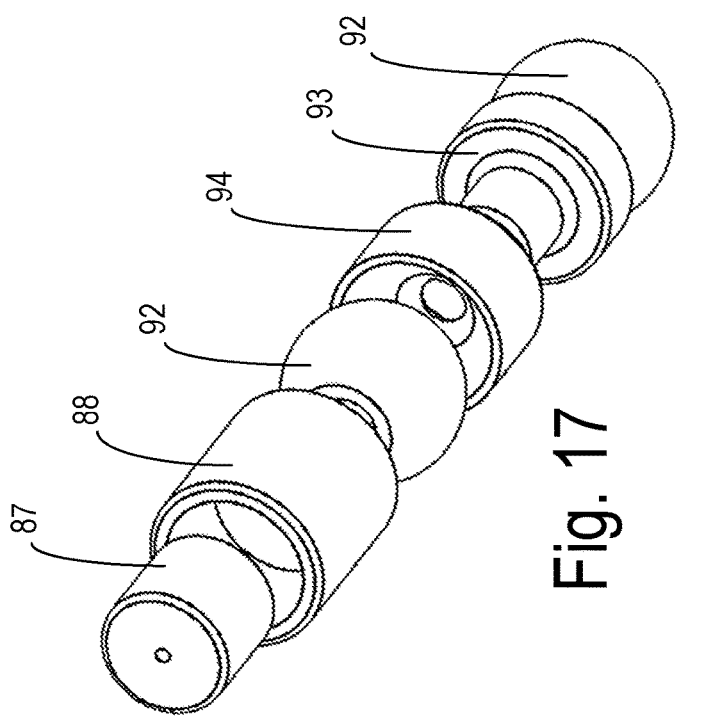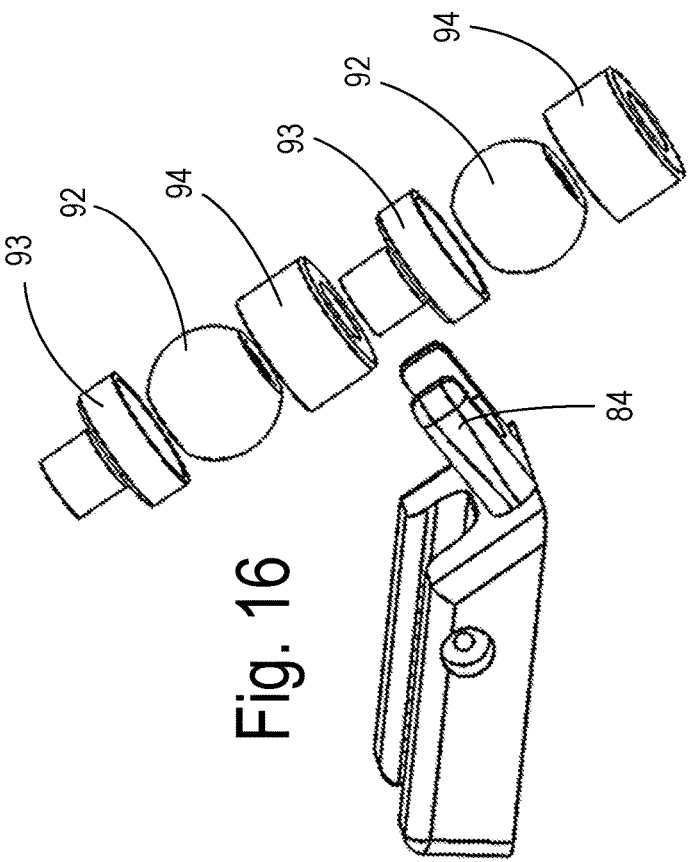

ARTICULATING STABILIZER ARM WITH ADJUSTABLE LENGTH

CROSS REFERENCE TO RELATED APPLICATIONS

This application is a continuation of PCT Application No. PCT/US2018/052842, filed Sep. 26, 2018, based on and claiming priority to U.S. Provisional Application No. 62/565,342, filed Sep. 29, 2017, both of which are incorporated herein by reference in their entirety.

BACKGROUND OF THE INVENTION

The present invention relates to a reusable flexible arm for stabilizing tissues during surgical procedures. In particular, in addition to providing both an elongated arm capable of a flexible state for conforming to a desired curvature and a rigid state for maintain a desired positioning, the invention further provides an adjustable length for the arm extending from its base.

A stabilizer arm is comprised of various intermediate links between a quick connection at the distal end and a mounting clamp at the proximal end for attachment to standard sternotomy retractors or other thoracic access devices. The quick connection can be easily mounted with disposable and/or reusable devices to manipulate (e.g., retract and stabilize) tissues at a surgical site. An example of a known stabilizer arm is commercially available as the Hercules™ Stabilizing Arm, sold by Terumo Cardiovascular Systems Corporation of Ann Arbor, Mich.

Since working space around a surgical site may become crowded, it is desirable for a stabilizer arm to have a low profile and to provide the capability to be easily adjusted to follow various contoured paths and then rigidly maintain the desired shape after being set up. An example of a known stabilizer arm is commercially available as the Hercules™ Stabilizing Arm, sold by Terumo Cardiovascular Systems Corporation of Ann Arbor, Mich. The stabilizer includes a lockable, articulating column wherein a central tensioning cable is strung through a series of links. When the cable is tensioned (e.g., by rotating a handle), the links move toward each other to interlock via a series of ball and socket joints. The column becomes rigid when the central cable is tensioned. Releasing the tension (e.g., by counter-rotating the handle) returns the column to the flexible state.

In the relaxed state, enough tension may be maintained to weakly remain in position as the column is adjusted to a desired configuration. The ball and socket joints are generally hemispherical so that side-to-side adjustment angles are available over a wide range. Nevertheless, the degrees of freedom to obtain a desired configuration have been somewhat limited because the overall length of the stabilizer arm has not been easily adjustable.

SUMMARY OF THE INVENTION

In one aspect of the invention, a stabilizer arm has a plurality of successive articulating links each having a central passage and a plurality of successive length-adjustable links each having a central passage. A tension cable extends through the central passages between a proximal one of the length-adjustable links and a distal one of the articulating links. A base member captures two adjacent length-adjustable links corresponding to a desired extension length of the arm from the base member. The base member is configured to be mounted to a supporting fixture. A control mechanism is movable between a retracted position and an extended position to selectably separate the two captured length-adjustable links, thereby adjusting a tension in the tension cable and a rigidity of the stabilizer arm.

BRIEF DESCRIPTION OF THE DRAWINGS

FIGS. 5 and 6 are perspective views of a pair of length-adjustable links of the stabilizer arm of FIG. 3.

FIG. 7 is a perspective view of the proximal portion of FIG. 4 is a pair of length-adjustable links expanded in the manner which applies tension to a tension cable.

FIGS. 15, 16, and 17 are exploded, perspective views of respective portions of the stabilizer arm of FIG. 14.

FIG. 18 is a cross-sectional view of a portion of the links of the stabilizer arm of FIG. 14.

DETAILED DESCRIPTION OF PREFERRED EMBODIMENTS

Figure 1:
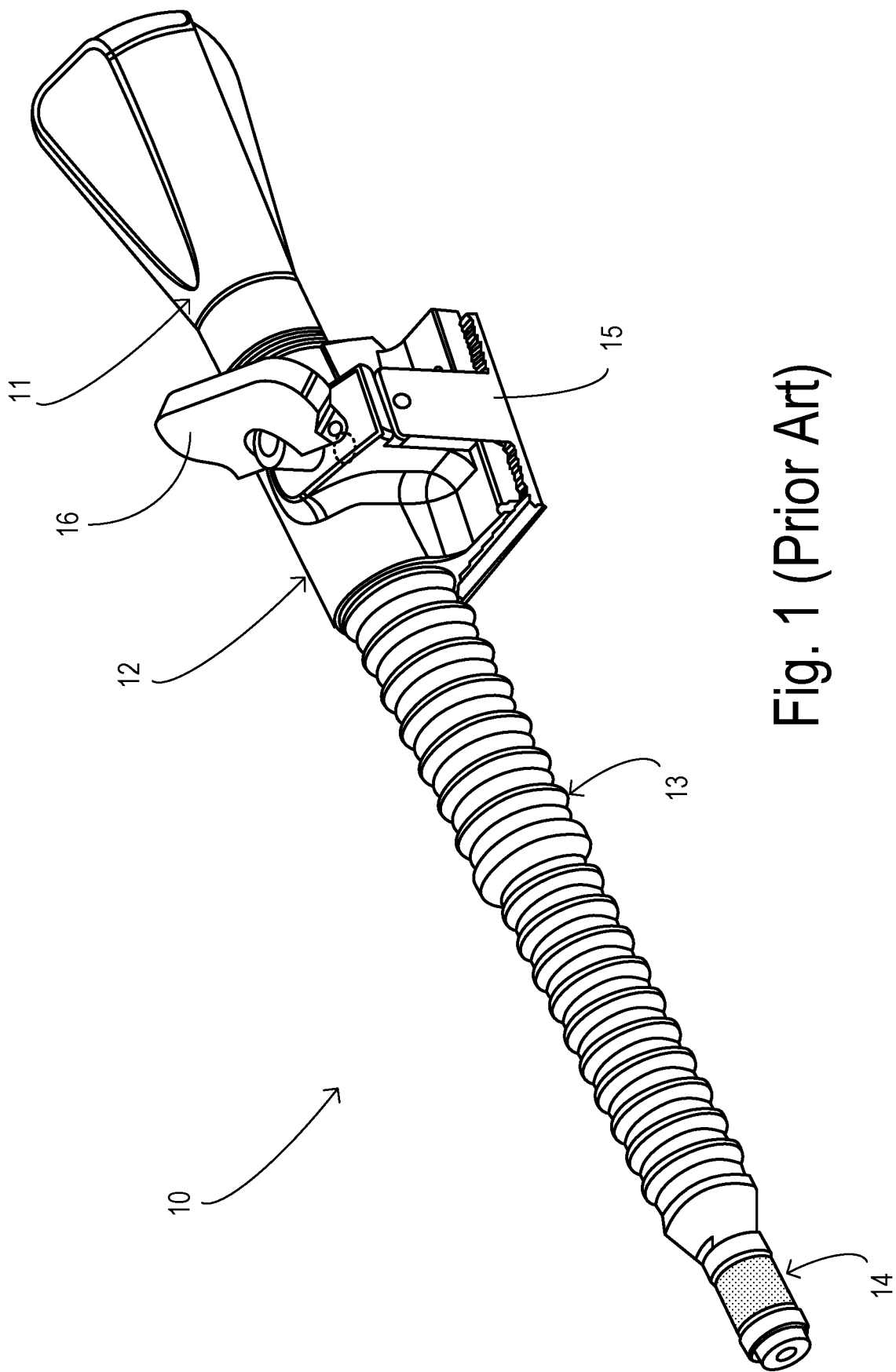
FIG. 1 is a perspective view of a prior art stabilizer arm in a straight configuration.

FIG. 1 shows a known stabilizing arm 10 with a handle 11, base 12, articulating section 13, and quick-connect mount 14. A clamp assembly 15 on base 12 is controlled by a butterfly handle 16 so that arm 10 can be attached to a fixture of a sternal retractor, for example.

Figure 2:
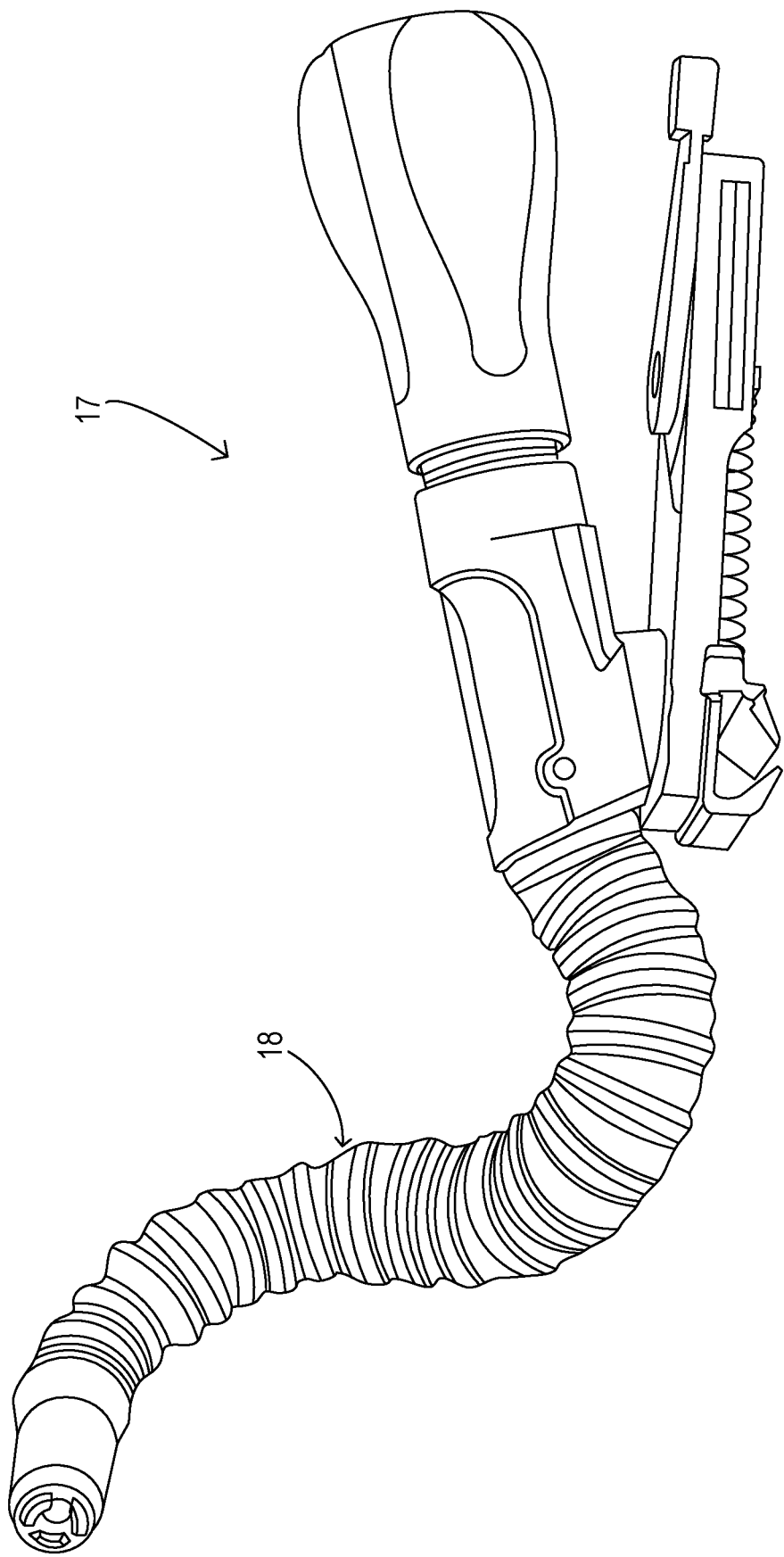
FIG. 2 is a perspective view of a prior art stabilizer arm in a curved configuration.

A tension cable extends from a proximal end of the stabilizing arm (e.g., from the base or handle) to the distal end (e.g., the quick-connect mount or a final fixed link in the adjustable linkage). A solid, stranded cable or a fiber resin can be used. In the example of FIG. 1, an internal mechanism adjusts tension in the cable in response to rotation of handle 11. Articulating section 13 has a plurality of nested, semi-spherical links which can be rotated within one another to provide bends in the direction in which section 13 extends. When the cable is sufficiently slack, the links are slidable but when the cable is tightened then the links bind together and section 13 retains a desired trajectory. FIG. 2 shows another example of a stabilizer arm 17 which an articulating column 18 which is locked into a curving configuration by tightening of a tension cable.

Figure 3:
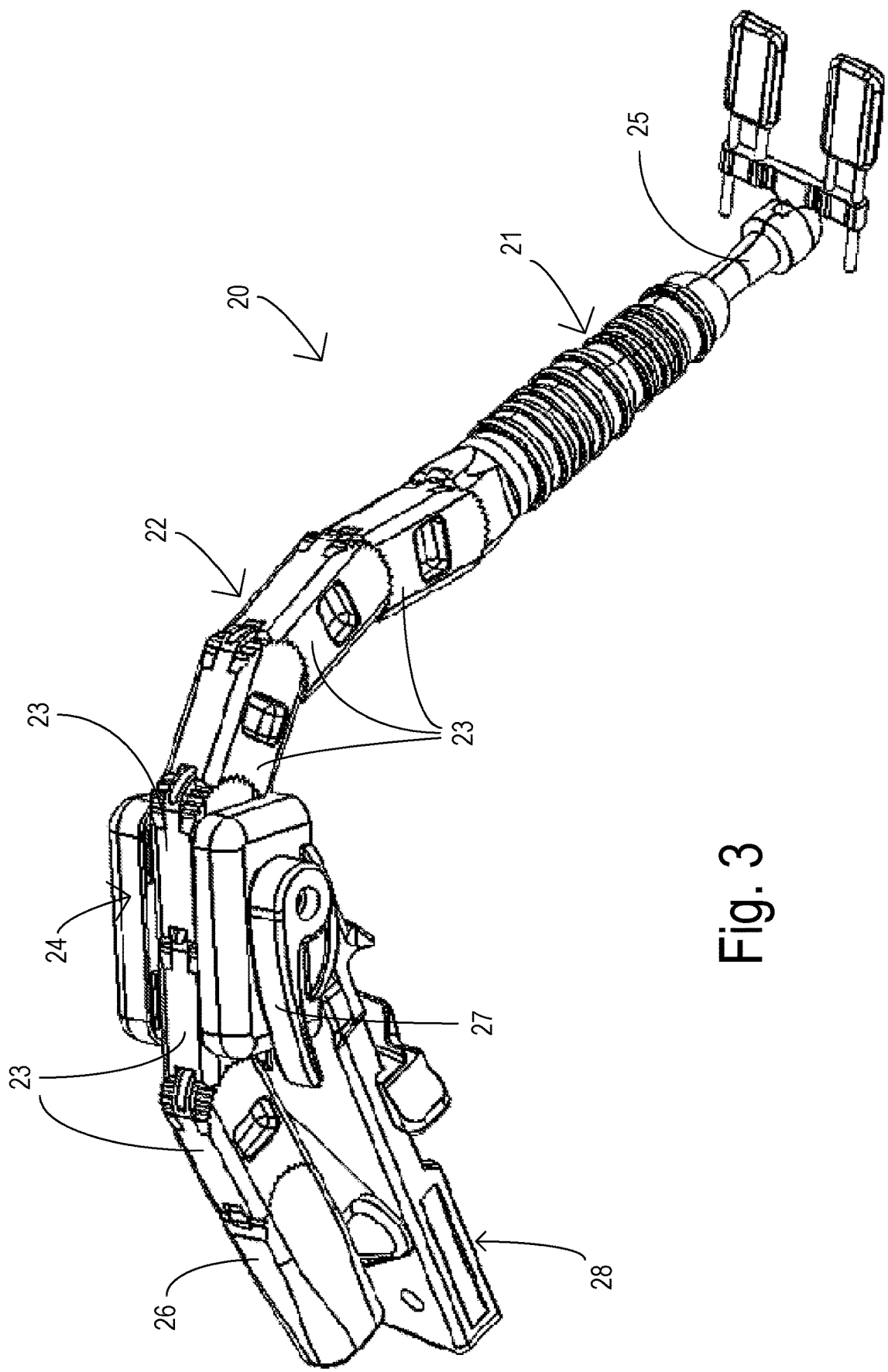
FIG. 3 is a perspective view of a first embodiment of a stabilizer arm according to the invention.
Figure 4:
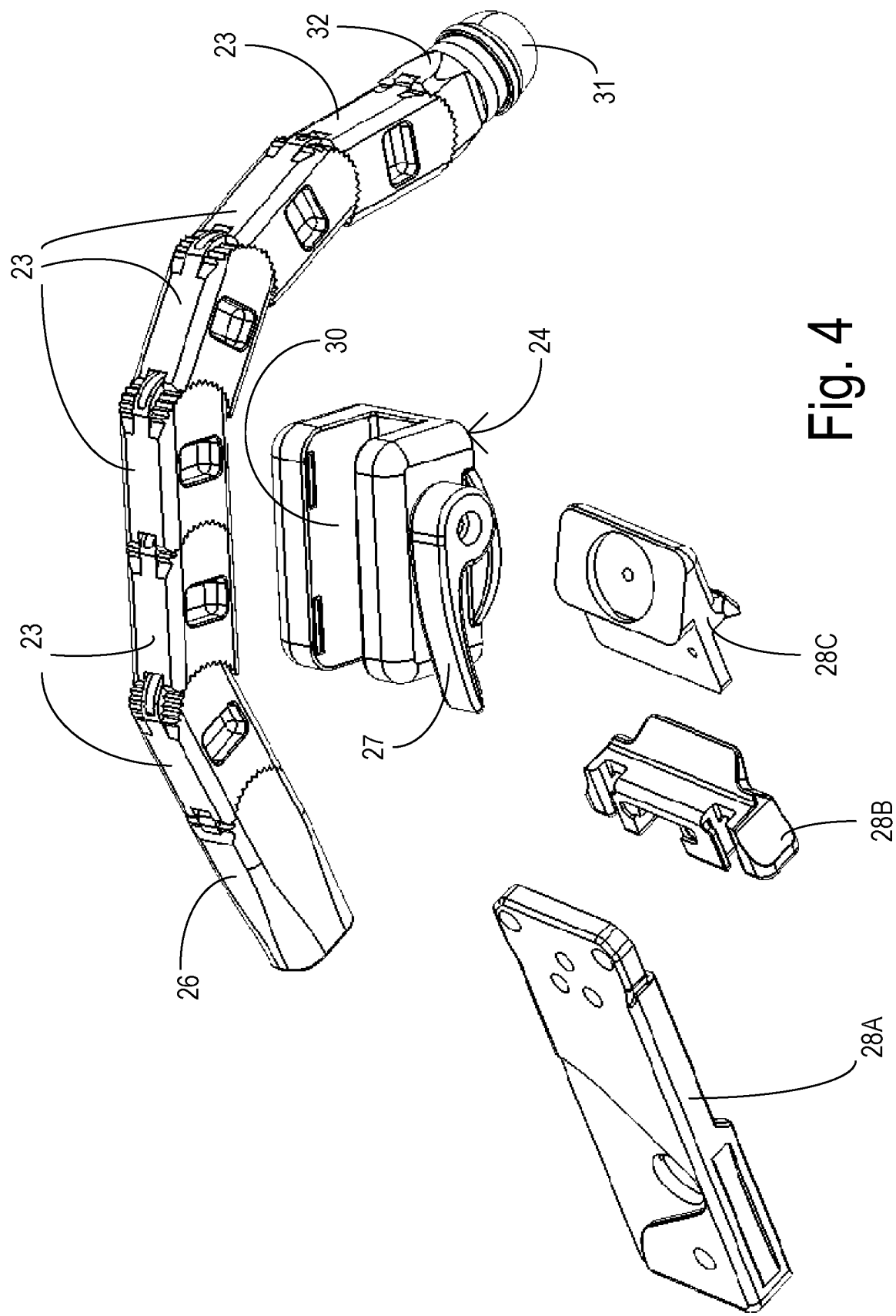
FIG. 4 is an exploded view of a proximal portion of the stabilizer arm of FIG. 3.
Figure 8:
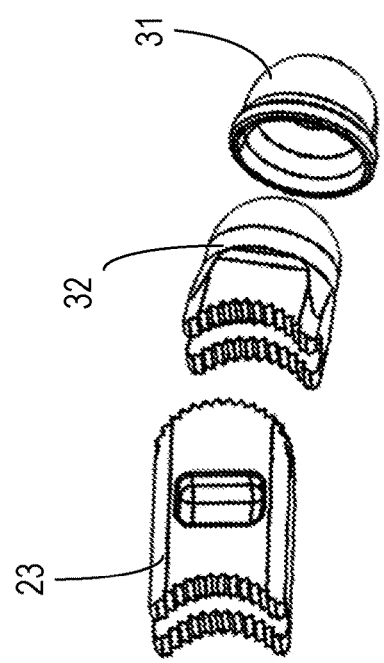
FIG. 8 is an exploded view of transitional links in the stabilizer arm of FIG. 3.

FIG. 3 shows a first embodiment of the invention wherein a stabilizer arm system 20 has an articulating arm portion 21 and a length adjustable arm portion 22. Individual links or segments in portion 21 are semi-spherical to bend in any desired direction. Individual links or segments 23 in portion 22 have flat, parallel sides and fit together in a tongue-ingroove fashion in order to articulate within a single plane. In addition, the flat sides have gripping features that cooperate with adjustable locking features in a mounting slot of a base member 24. A tension cable (not shown) extends internally through the links between an end shaft 25 (e.g. carrying a quick-connect mechanism for receiving a retraction tool) and a proximal anchor segment 26. Tension in the cable can be applied or released using a lever 27 on base member 24 as explained in more detail below. A transition link 32 is adapted to join a distal-most one of links 23 of length-adjustable portion 22 with a first link 31 in articulating portion 21 (see FIGS. 4 and 8).

Base member 24 is attached to a mounting structure 28 which is configured to attach to a sternal retractor frame as known in the art. As shown in the partially exploded view in FIG. 4, base member 24 has an upper mounting slot 30 arranged to grasp two adjacent links 23. Mounting components 28A and 28B attach to a sternal retractor frame in a conventional manner using a locking lever (not shown). An adapter element 28C is attached between component 28A and a bottom surface of base member 24.

FIGS. 5 and 6 shows links 23 in greater detail. Left and right lateral sides 35 and 36 of each link 23 have indentations or index notches 37 and 38, respectively, which are adapted for grasping by matching features that selectably project into slot 30 in base member 24. A distal end of each link 23 has a curved tongue 40 extending in a distal direction to be received in a matching groove 41 on a proximal end of an adjacent link 23. Arched surfaces on both lateral sides of tongue 40 and groove 41 are provided with matching teeth 42 and 43 which help to fix adjacent links 23 in place. Tongue 40 and the main body of each link 23 have an internal bore 44 for receiving the tension cable.

FIG. 7 shows a spring cap 45 which is clamped over one end of the tension cable and which is mounted within proximal anchor segment 26. Length adjustment is obtained by unlocking internal locking pins within base member 24 by appropriately positioning lever 27, so that links 23 are released and can be slid longitudinally within slot 30 until a desired adjacent pair of links 23 (i.e., matching a selected overall length from base member 24 to the distal end of the arm) are aligned with the locking pins. With the locking pins registered within indentations 38 of adjacent links 23, rotation of lever 27 in the appropriate direction causes the locking pins to spread apart longitudinally. The longitudinal separation is transferred to links 23 so that the pair of links moves longitudinally apart as shown at arrows 46. The separation causes increased tension in the tension cable, which results in all other links being compressed against their adjacent neighbors with sufficient force to bind them rigidly together. The action of the locking pins simultaneously locks the stabilizer arm in place within slot 30.

Figure 9:
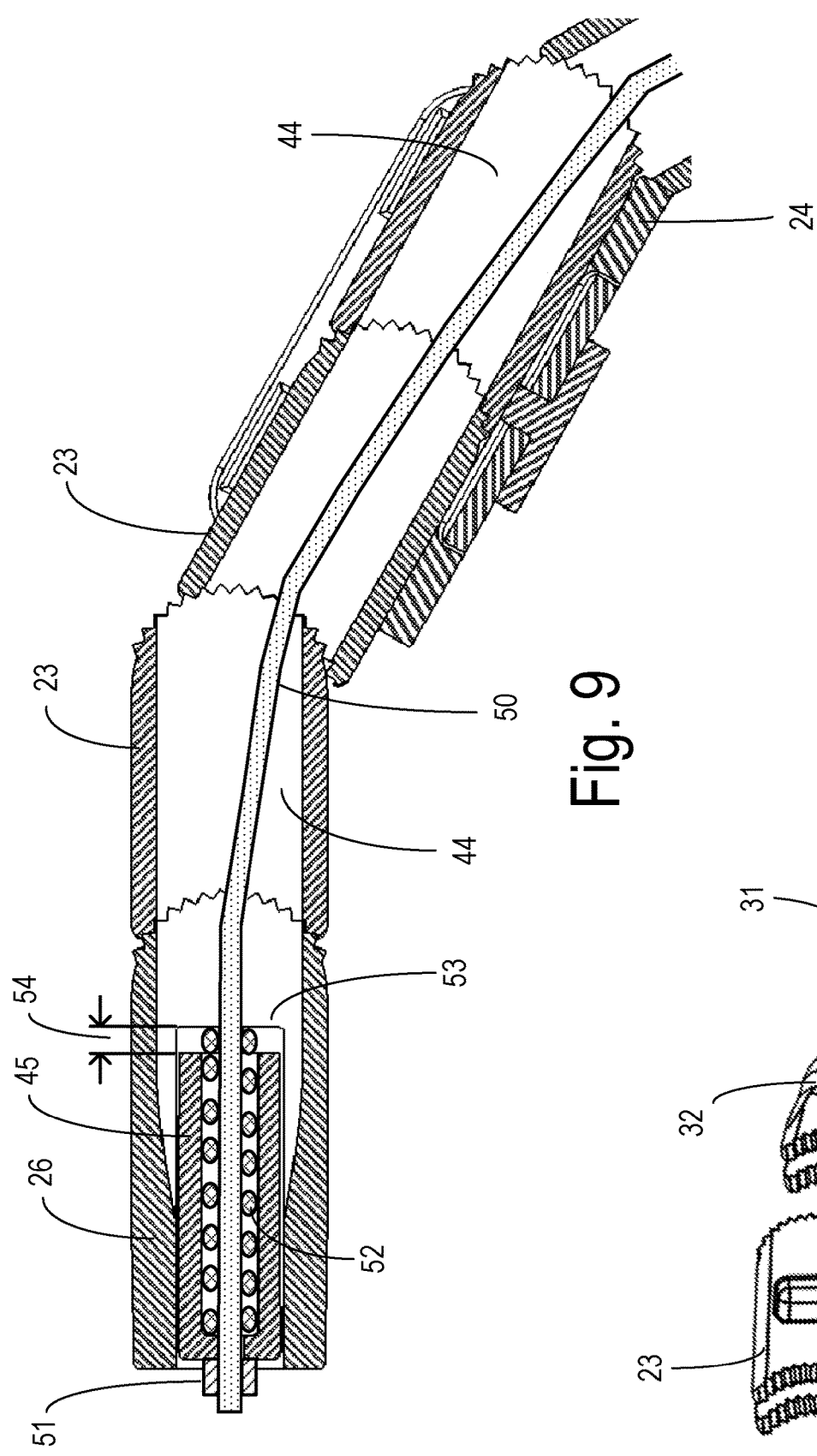
FIG. 9 is a cross-sectional view of a proximal end of the stabilizer arm of FIG. 3.

The cross section of FIG. 9 shows spring cap 45 slidably mounted within a socket in proximal anchor segment 26. Tension cable 50 passes through end-to-end bore 44 and has a proximal end joined to cap 45 by a crimped retainer 51. A spring 52 is disposed within cap 45 to bear against a proximal end of cap 45 at one end and against a socket bottom wall 53 of segment 26 in order to apply a tension pre-load to cable 50. The pre-load tension is configured to hold all the links loosely together to assist with adjusting the stabilizer arm to a desired shape (curvature and length) before applying full tension using lever 27. The spring force creates a gap 54 between cap 45 and wall 53 so that the pre-load force can be overcome manually as necessary for adjusting the shape.

Figure 11:
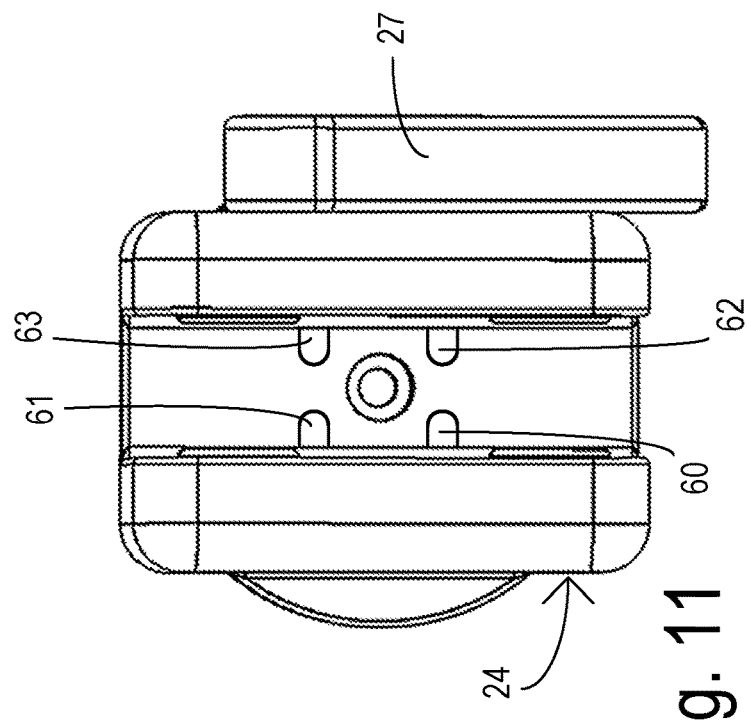
FIGS. 10 and 11 are a perspective view and a top view, respectively, of the base member the stabilizer arm of FIG. 3.
Figure 10:
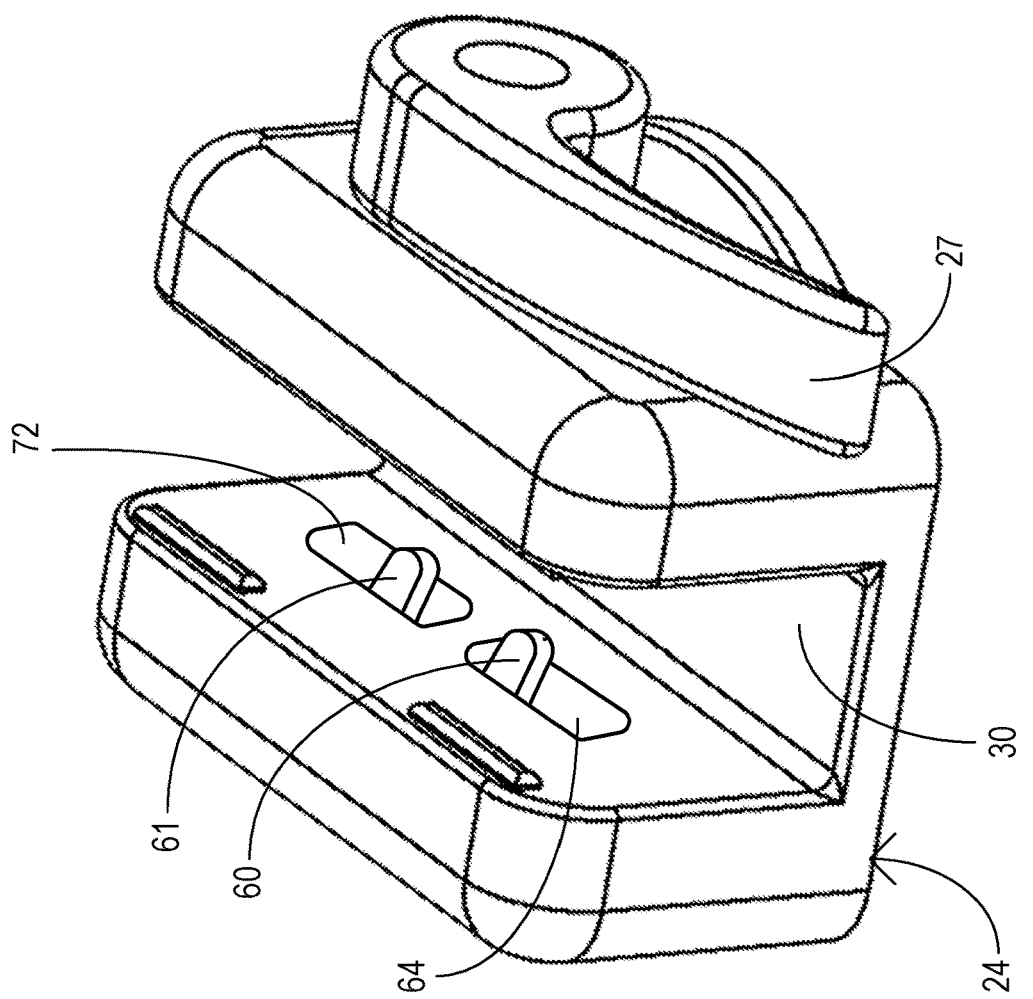
Figure 12:
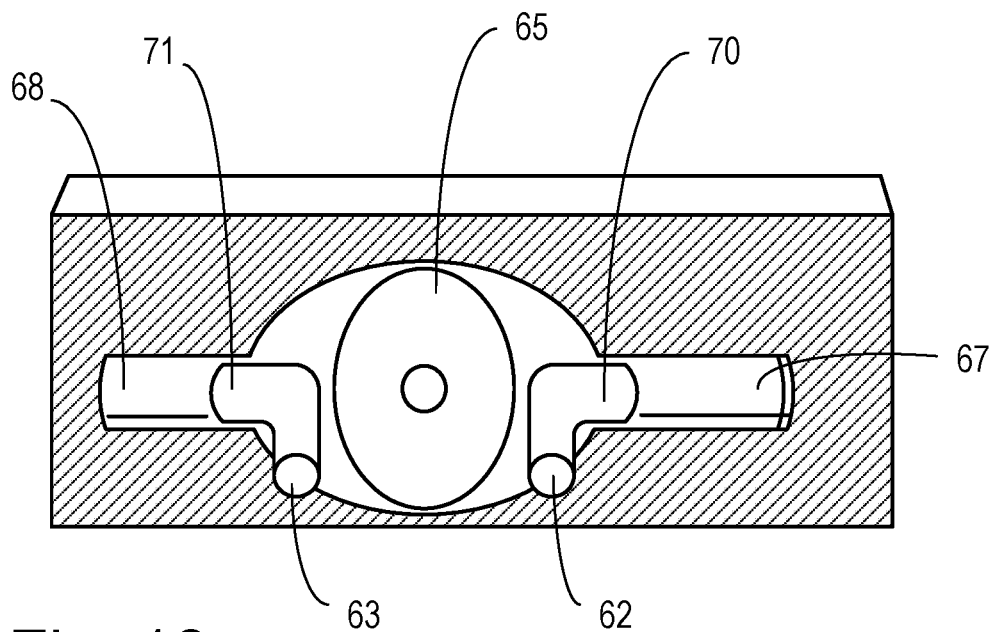
FIG. 12 is a cross-sectional view of a first embodiment of a control mechanism of the invention.

FIGS. 10 and 11 show locking pins 60 and 61 on one side of slot 30 and locking pins 62 and 63 on the other side of slot 30. Pins 60 and 61 are longitudinally slidable within internal tunnels 64 and 72, respectively. FIG. 12 is a cross-sectional view of a side wall of base member 24 revealing an elliptical cam 65 disposed in an internal cavity 66. Cam 65 is rotationally driven by lever 27. It bears against locking pins 62 and 63 which are slidable within respective tunnels 67 and 68 extending from cavity 66. The bottoms of tunnels 67 and 68 may be sloped so that the outward ends of pins 62 and 63 retract into the wall when they are closest together (thereby allowing links 23 to freely slide through slot 30). When cam 65 is rotated via lever 27, they spread apart along tunnels 67 and 68 to separate the captured links.

Figure 13:
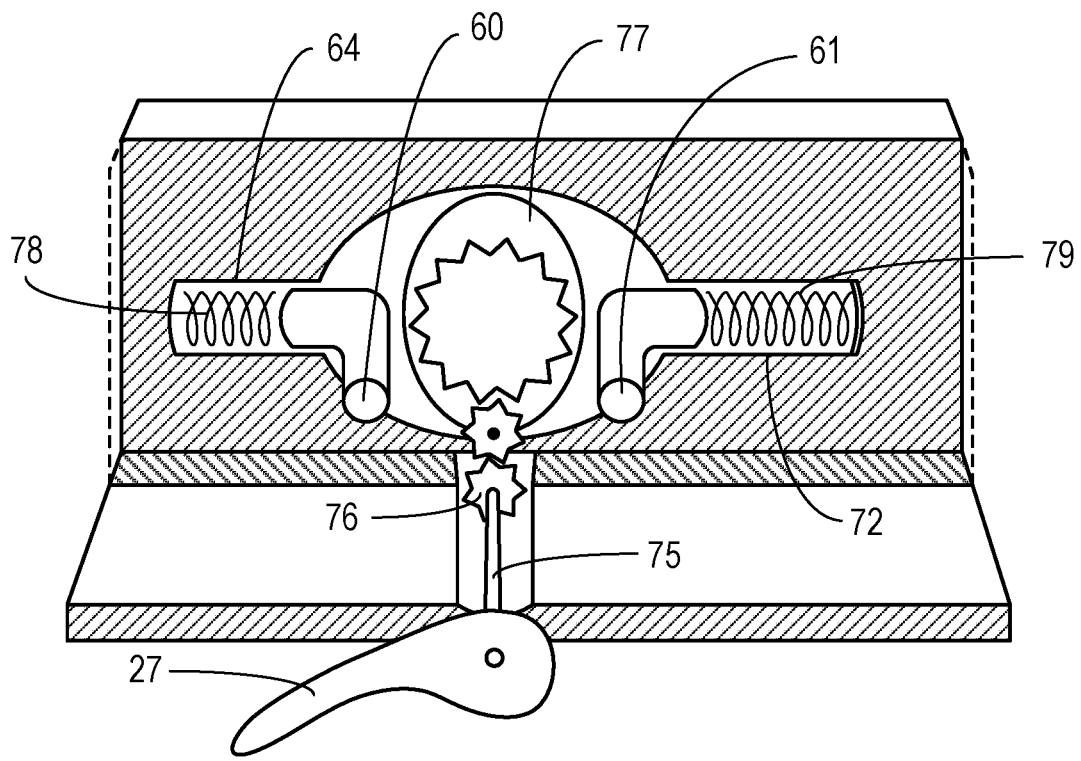
FIG. 13 is a cross-sectional view of a second embodiment of a control mechanism of the invention.

FIG. 13 shows an embodiment for transferring motion from lever 27 to the far side of base member 24 using a shaft 75 and gearset 76 to transfer rotation to an elliptical cam 77 which drives locking pins 60 and 61. Springs 78 and 79 are added in tunnels 64 and 72 to urge pins 60 and 61 against cam 77.

Figure 14:
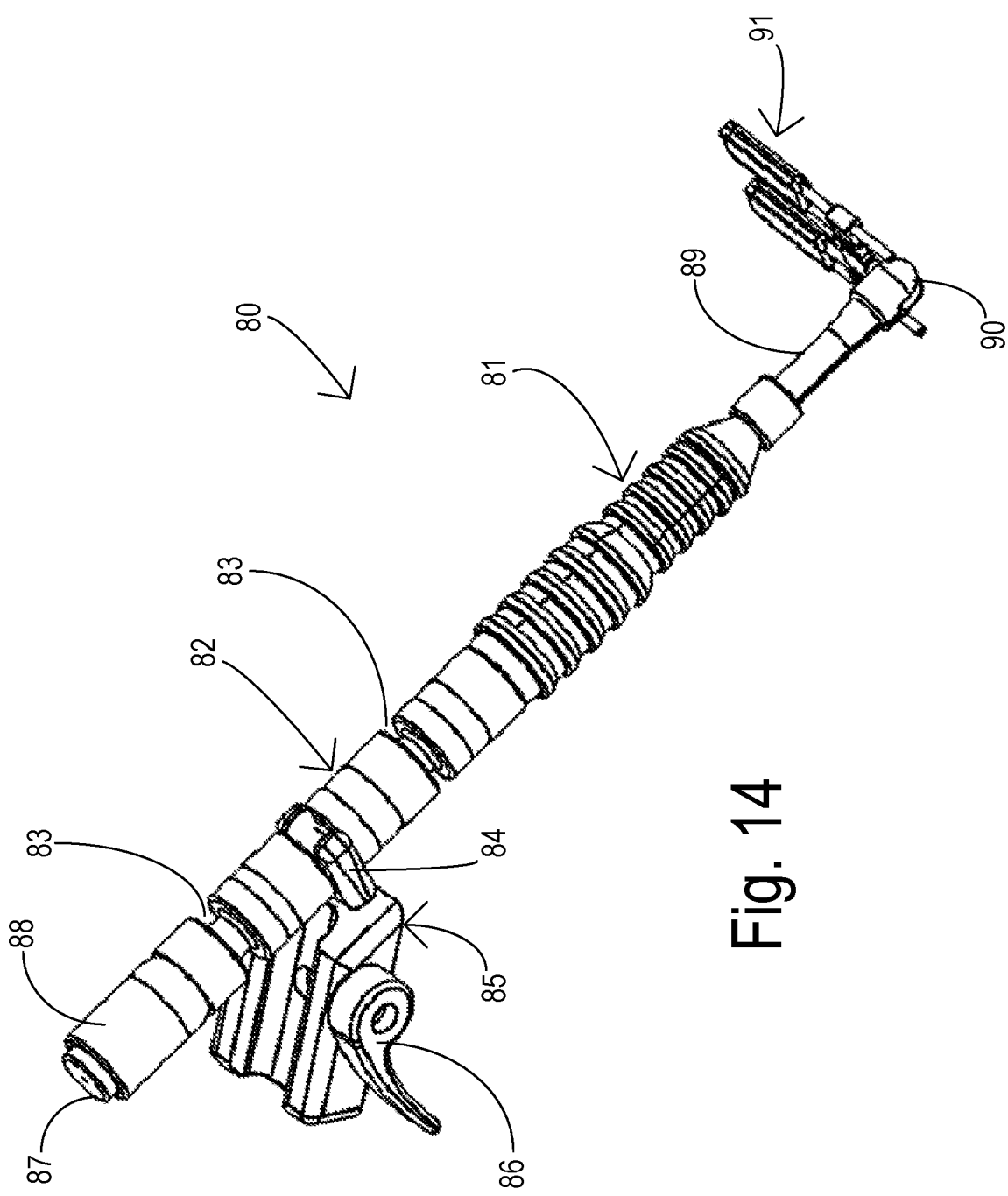
FIG. 14 is a perspective view of an alternative embodiment of a stabilizer arm of the invention.
Figure 15:
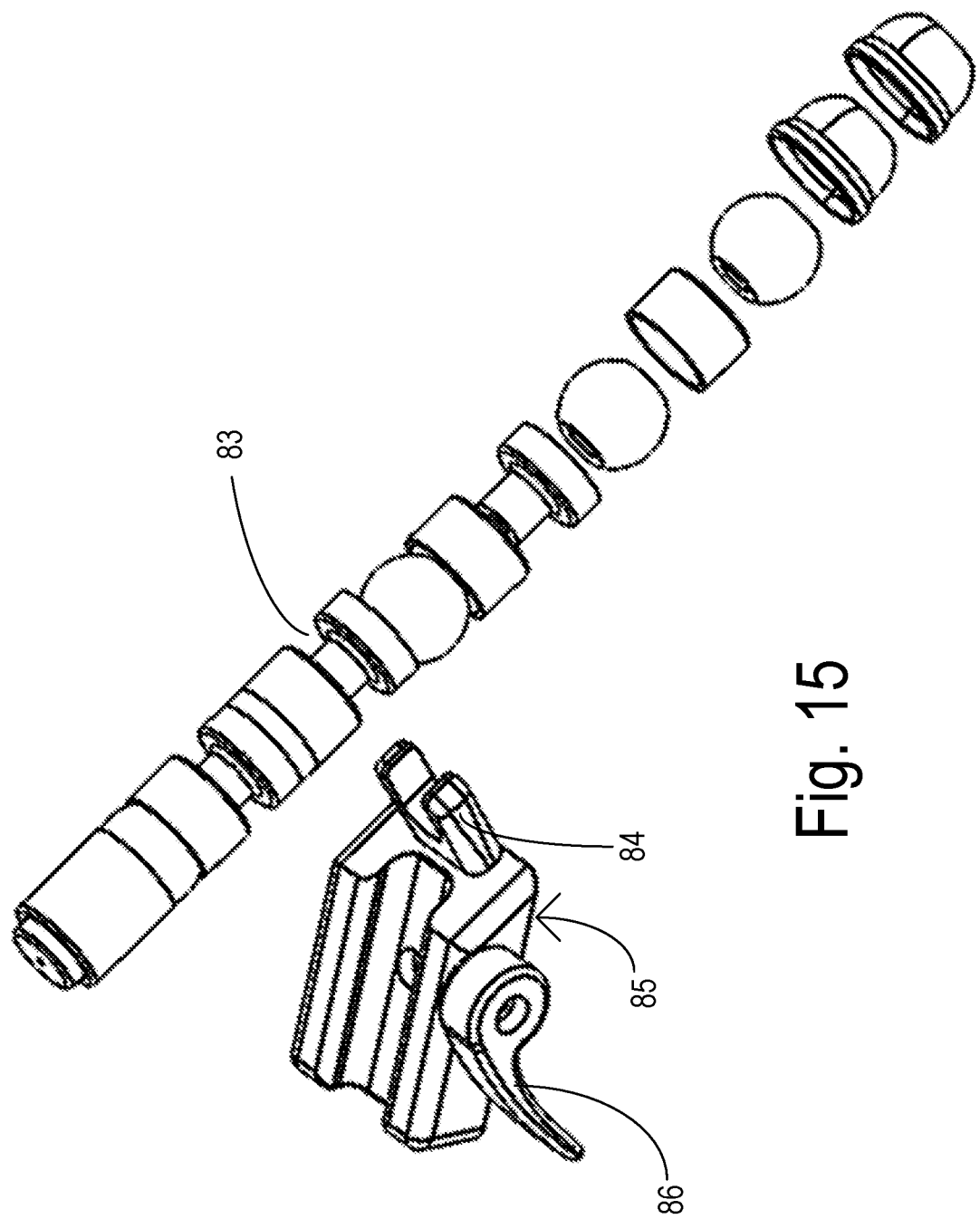

FIG. 14 shows an another embodiment of a stabilizer arm system 80 having an articulating portion 81 and a length-adjustable portion 82. Portion 82 has a plurality of spaced neck regions 83 where it can be seized by a fork-like clamp 84 on a base member 85 under control of a lever 86. An internal tension cable is attached at a proximal end to a cap 87 held in an anchor segment 88 and is attached to an end shaft 89 at a distal end. End shaft 89 has a quick connect 90 for holding a valve rake or other accessory 91.

Fork clamp 84 is expandable in the axial direction by a mechanism (not shown) under control of lever 86. Portion 82 is composed of a series of ball segments 92, telescoping segments 93, and spacers 94 (all defining a continuous central bore for receiving the tension cable). Telescoping segments 93 each has a concave cup portion with a diameter large enough to receive a ball segment 92. Each cup portion has an inner hole and extends into a hollow cylindrical shaft or tube that is slidably received in a central bore of an adjacent spacer 94. Spacers 94 likewise have concave cups for receiving adjacent ball segments 92. By axially expanding a fork clamp 84 within any one of the neck regions 83, a gap 95 as shown in FIG. 18 opens up which applies tension to the tension cable. End cap 87 is slidably received in an end recess of anchor segment 88. Another gap 96 within the recess between cap 87 and segment 88 can be provided with a spring or other compression element (not shown) to provide a preload tension to the cable (not shown) which is rigidly attached to cap 87.

What is claimed is:
1. A stabilizer arm system comprising:
  a stabilizer arm comprising
    a plurality of successive articulating links each having a central passage;
    a plurality of successive length-adjustable links each having a central passage; and
    a tension cable extending through the central passages between a proximal one of the length-adjustable links and a distal one of the articulating links;
  a base member capturing at least portions of two of the plurality of length-adjustable links corresponding to a desired extension length of the arm from the base member, wherein the base member is configured to be mounted to a supporting fixture; and
  a control mechanism movable between a retracted position and an extended position to selectably separate the captured length-adjustable links, thereby adjusting a tension in the tension cable and a rigidity of the stabilizer arm, wherein the length-adjustable links have opposite lateral sides, wherein each length-adjustable link has an index notch in a lateral side configured to engage the control mechanism.

2. The stabilizer arm system of claim 1 wherein the base member includes a slot longitudinally receiving the at least portions of two of the plurality of length-adjustable links so that the index notches of the two length-adjustable links engage the control mechanism within the slot.

3. The stabilizer arm system of claim 2 wherein the control mechanism comprises movable pins, wherein the movable pins are captured in the index notches.

4. The stabilizer arm system of claim 3 wherein the control mechanism further comprises a lever for adjusting a longitudinal separation between the index notches.

5. The stabilizer arm system of claim 4 wherein the lever further controls a penetration of the movable pins into the slot, thereby retaining the length-adjustable links into the slot.

6. The stabilizer arm system of claim 1 wherein the length-adjustable links each includes an arched end for nesting with an arched end of an adjacent length-adjustable link.

7. The stabilizer arm system of claim 6 wherein adjacent arched ends of the length-adjustable links have matching teeth.

8. The stabilizer arm system of claim 6 wherein each pair of adjacent arched ends includes a tongue in groove joint.

9. The stabilizer arm system of claim 1 wherein the length-adjustable links include an anchor segment adapted to fasten the tension cable.

10. The stabilizer arm system of claim 1 wherein the articulating links each has a semi-spherical shape for engaging an adjacent articulating link.

11. The stabilizer arm system of claim 1 further comprising an end shaft attached to the distal one of the articulating links and having a quick connect fitting configured to mount a surgical retractor device.

12. The stabilizer arm system of claim 1 wherein the control mechanism includes a spring applying a preload tension to the tension cable.

* * * * *